United States Patent [19]

Schuler

[11] 3,994,714

[45] *Nov. 30, 1976

[54] METHOD FOR SELECTIVE HERBICIDAL TREATMENT OF BARLEY CULTURES

[75] Inventor: Max Schuler, Arlesheim, Switzerland

[73] Assignee: Sandoz Ltd., Basel, Switzerland

[*] Notice: The portion of the term of this patent subsequent to Feb. 11, 1992, has been disclaimed.

[22] Filed: Dec. 23, 1974

[21] Appl. No.: 535,297

Related U.S. Application Data

[63] Continuation-in-part of Ser. No. 275,560, July 27, 1972, Pat. No. 3,865,571, which is a continuation-in-part of Ser. No. 882,293, Dec. 4, 1969, abandoned, which is a continuation-in-part of Ser. No. 743,589, July 10, 1968, abandoned, which is a continuation of Ser. No. 583,108, Sept. 29, 1966, abandoned, and Ser. No. 583,109, Sept. 29, 1966, abandoned.

[30] Foreign Application Priority Data

Oct. 28, 1965 Switzerland.................. 14919/65
July 28, 1966 Switzerland.................. 10954/66

[52] U.S. Cl. .................................................. 71/120
[51] Int. Cl.² ............................................ A01N 9/20
[58] Field of Search ................................... 71/120

[56] References Cited

UNITED STATES PATENTS 2,655,445   10/1953   Todd ..................................... 71/120
2,655,447   10/1953   Todd ..................................... 71/120
3,288,851   11/1966   Martin et al. ........................ 71/120

*Primary Examiner*—Lewis Gotts
*Assistant Examiner*—Catherine L. Mills
*Attorney, Agent, or Firm*—Gerald D. Sharkin; Richard E. Vila

[57] ABSTRACT

N-(3-chloro-4-methoxyphenyl)-N',N'-dimethylurea of the formula:

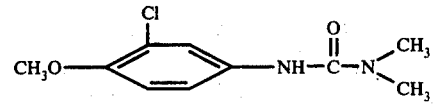

is disclosed as possessing a surprising selective herbicidal activity. A method is disclosed for selectively combating weeds in a cereal locus and in particular a barley locus, which comprises applying to the locus to be protected from weeds, a dosage of from 2 to 10 kilograms per hectare of the above compound.

5 Claims, No Drawings

METHOD FOR SELECTIVE HERBICIDAL TREATMENT OF BARLEY CULTURES

This application is a continuation-in-part of our copending application Ser. No. 275,560, filed July 27, 1972, now U.S. Pat. No. 3,865,571 which in turn is a continuation-in-part of our now abandoned application Ser. No. 882,293, filed Dec. 4, 1969, which is in turn a continuation-in-part of our application Ser. No. 743,589, filed July 10, 1968 and now abandoned, which in turn is a continuation by consolidation of our applications Ser. Nos. 583,108 and 583,109, both filed Sept. 29, 1966 and both now abandoned.

The present invention relates to a method of selectively combating weeds in a cultivated plant locus and more specifically to a method of selectively combating weeds in a cereal, e.g. wheat, locus or a carrot locus.

The use of aryl urea derivatives for combating weeds has been known for sometime. As long ago as 1946, H. E. Thompson et al. reported plant growth inhibition by aryl urea derivatives [Botan. Gaz. 107 476–507 (1946)].

Some time later, the compound "monuron" (trade name for N-(4-chlorophenyl)-N',N'-dimethylurea) was introduced as a total herbicidal. Following the commercial introduction of monuron, a succession of related compounds were also made available as total herbicides. Of such related compounds "fenuron" (trade name for N-phenyl-N',N'-dimethylurea) and "diuron" (trade name for N-(3,4-dichlorophenyl-N',-N'-dimethylurea) may be mentioned as the most important.

These compounds are characterised by an N',N'-dimethyl residue. Further aryl urea derivatives were later developed having instead of an N',N'-dimethyl residue of the earlier total herbicides, an N-methoxy-N-methylamino residue.

Attention however was still concentrated on the earlier total herbicides, and eventually it was discovered that such herbicides at low dosages, under the right conditions and in certain crops did in fact operate to selectively combat weeds in pre-emergence treatment of the crop locus. It was, and still is, of course recognised, however, that such selectivity is accompanied by the risk of considerable crop damage, e.g. in the case of heavy rainfall, unsuitability of the soil and over dosing, since the earlier aryl urea are basically total herbicides. Moreover, as is well known, a crop plot, having been surface treated with the total herbicides, cannot be replanted within at least one year and sometimes 2 years, without serious risk of loss of the subsequent crop owing to the high residual effect of the aryl urea. Indeed, at present, their main practical use is in soil sterilisation.

The selective mode of action of the earlier aryl ureas in the pre-emergence treatment of crops has been explained on the basis of their low water solubility and their tendency to remain in the surface layers of the soil. Since they are highly effective at killing young seedling plants following uptake thereof through the roots from the soil, weeds, which are frequently shallow germinating and have at least some roots near the soil surface will be eradicted by the herbicide treated surface layers. The root zones of crop plants on the other hand, which are the herbicide sensitive region of the plant, hardly contact the herbicide treated surface layer since they are generally disposed deeper in the soil below said layer. It will be appreciated therefore that by such "mechanical" selectivity, the crop plant may survive, its stem being relatively herbicide insensitive and passing through the herbicide treated surface layer, while the weeds are eradicated. It will also be appreciated however, that such mechanical selectivity may be highly precarious especially in locations susceptible to heavy rainfall whereby the herbicide may be leached down through the soil to the herbicide sensitive roots of the crop plant or be washed away into localised pools where their total herbicidal activity may be effectively exercised. Moreover, such mechanical selectivity is subject to further serious limitations in the case, for example, of the herbicide sensitive zones of the crop plants and weed species being disposed at similar depths in the soil. This is in fact typical of weed grass infested cereal crops, particularly wheat crops where both the weeds and the crop are members of the grass family.

It is to be understood that some herbicides are now known having a selective mode of action which can only be explained on the basis of physiological tolerance of the crop plant to the herbicide. A well known example of such selectivity, which relies on a "biological" as opposed to a mechanical selective mode of action, is the case of the herbicide "simazine" (trade name for 2-chloro-4,6-bis-ethylamino-1,3,5-triazine) in maize. Such herbicides are however relatively uncommon.

It has now surprisingly been found that a certain aryl urea having an N',N'-dimethyl residue exercises an excellent degree of biological selectivity in cereals and carrots, and moreover has a relatively shorter residual effect than the earlier total herbicides. This compound is one of a series of aryl ureas that have been disclosed in U.S. Pat. No. 2,655,445.

Accordingly, the present invention provides a method of selectively combating weeds in a cereal or carrot locus to be protected from weeds which comprises treatment of the locus with N-(3-chloro-4-methoxyphenyl)-N',N'-dimethylurea of formula I,

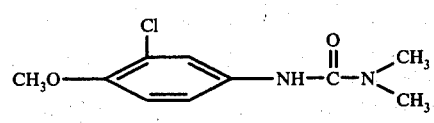

in an amount of from 2 to 10 kilograms per hectare of locus.

It is to be understood that by cereal locus is meant a locus to be or having been sown with cereal seed and the method of the invention embraces both pre- and post-emergence treatment of the cereal crop. Similarly, by carrot locus is meant a locus to be or having been sown with carrot seed and the method of the invention embraces both pre- and post-emergence treatment of the carrot crop.

The method is particularly applicable to treatment of the locus after the cereal or carrot seed, as the case may be, has been sown.

Examples of cereals contemplated within the scope of the method of the invention are winter and summer wheat, winter and summer rye, and winter and summer barley.

As is well known, an effective and safe method of combating weeds, particularly weed grasses, in wheat is particularly sought after in the art and thus the treatment of a wheat locus is a preferred embodiment of the invention. Examples of weed grasses widespread in wheat and against which the method of the present invention is effective are *Bromus tectorum* (cheat grass) and *Lolium multiform* (animal rye grass). It is particularly notable that even today, no effective selective control of *Bromus tectorum* in wheat is available.

The compound can be applied by conventional techniques to the particular locus at a dose of up to about 10 kilogram per hectare without significantly affecting the cereal or carrot crop growth. The extent of the dose at which the compound may be applied to allow selective growth of the cereal and carrot crops is such that weed growth can be very successfully controlled, even at a dose as low as about 2 kilogram per hectare.

In general, a preferred dose is between 3 to 6 kilogram per hectare, although in the case of carrots, in some cases, a higher dose may be desirable. As will be readily appreciated by those in the art, the particular dose selected will vary with such factors as the type of soil, climatic conditions and the degree and type of infestation.

The compound has an exceptional and practical effect spectrum. For example, it has been found that the compound is effective against such important species as *Agrostis alba*, *Alopecurus spp.*, *Apera spica-venti*, *Avena fatua*, *Lolium perenne* and *Plantago major*. The activity of the compound against *Plantago major* is indeed unexpected in that the literature on the subject indicates that N-aryl-N',N'-dimethylureas are practically ineffective against this weed (see, for example E. K. Woodford and S. A. Evans, "Weed Control Handbook," 3rd Ed. 1963, page 194; and Ph. Jussiaux and R Pequinot, "Mauvaises Herbes", Paris 1962, page 117).

The compound may be applied before or after germination of weeds, or before sowing of the cereal or carrot seeds, or simultaneously with the sowing of the cereal or carrot seeds, or after the cereal or carrot seeds have been sown, or after germination of the cereal or carrot seeds.

The compounds of the formula I may be produced in known manner, for example, by starting with 3-chloro-4-methoxyphenyl-isocyanate and dimethylamine, or starting with N,N-dimethylcarbamoylchloride and 3-chloro-4-methoxyaniline.

The following examples A and B illustrate production of the compound of formula I:

EXAMPLE A 73.4 g (0.4 mol) of 3-chloro-4-methoxyphenyl isocyanate (boiling point 79°–89° C/0.2 mm of Hg) are added dropwise at 5°–10° C over ¾ to 1 hour to 45 g of 40% by weight aqueous dimethylamine solution (corresponding to 0.4 mol of dimethylamine); an exothermic reaction takes place and, as the reaction proceeds, the product is continuously precipitated in crystalline form. The crystalline precipitate is filtered with suction, washed with a little water and dried at 50°–70° C in a water pump vacuum. The compound of formula I is obtained in the form of colourless crystals having a melting point 123°–125° C with a yield of 82.5 to 87 g (90 to 95% of theory). After recrystallization from ethanol, colourless crystals of melting point 126°–127° C are obtained.

The compound of formula I is likewise obtained when gaseous dimethylamine is introduced to saturation point into a solution of 0.1 mol of 3-chloro-4-methoxyphenylisocyanate in 200 ml of anhydrous ether at 20° C while stirring well and cooling, the resulting reaction product being filtered off with suction and dried.

EXAMPLE B 63 g of 3-chloro-4-methoxyaniline (0.4 mol) and 42 g of triethylamine are dissolved in 300 ml of dimethylformamide. 45 g (0.418 mol) of N,N-dimethylcarbamoylchloride are stirred dropwise into the resulting solution over 20–30 minutes, care being taken by cooling that the temperature, which initially should be 20°–25° C does not rise above 30°–35° C. Shortly after the reaction has commenced, the resulting triethylamine hydrochloride begins to precipitate. After all the N-N-dimethylcarbamoylchloride has been added, stirring is effected for a further 4 to 8 hours at 30°–35° C and the triethylaminehydrochloride is then removed from the reaction solution by suction. Dimethylformamide is distilled off at 0.02 to 0.2 mm of Hg at a bath temperature of 35°–45° C. The crystalline residue is stirred with 250–400 ml of water whereupon the required product crystallizes out. Filtering with suction is effected, washing with a little water is carried out and drying is effected at 50°–80° C in a water pump vacuum.

The compound of formula I is obtained in the form of colourless crystals, which, depending on the purity of the amino compound used, may be slightly beige to brownish, of melting point 121°–124° C with a yield of 78–85 g (83–93% of theory). By recrystallizing from ethanol there are obtained colourless crystals of melting point 125°–127° C.

The compound of formula I may be applied to the particular locus by conventional techniques. Thus, the compound may be provided as a concentrate for dilution with conventional herbicidal diluents. Suitable preparation forms include solutions, emulsions, suspensions, dusting powders, strewing agents and granulates. A suitable diluted aqueous suspension or emulsion ready for use contains 0.005–1% by weight of the compound I, and the suspension or emulsion may, if desired, contain known agents for facilitating distribution and increasing the adhesive power and resistance to rain.

Application of preparations containing the compound of formula I may be effected by firstly emulsifying or suspending the preparation in water and then sprinkling plants to be treated. Application may be effected before or after germination of weeds or crop. Application may furthermore be effected by dusting weeds to be destroyed, or by the direct application of the preparation containing the compound of formula I, said preparation then conveniently being in the form of a dusting or strewing agent or granulate. If necessary, the preparation may be worked into the soil.

In the following Examples I to IX some possibilities of producing suitable preparations containing the compound of formula I and their constituents are described.

EXAMPLE I

70 Parts by weight of the compound of formula I together with 29 parts by weight of an inert solid carrier, consisting of a mixture of 2 parts of kaolin, one part of diatomaceous earth and one part of talcum, and also one part by weight of an adhesive commonly used for this purpose are ground to a fine powder in a ball mill; the resulting powder may be used as a dusting agent.

EXAMPLE II

20 Parts by weight of the compound of formula I together with 72 parts by weight of an inert solid carrier mixture (consisting of ⅔ of diatomaceous earth and ⅓ of kaolin), 6 parts by weight of isooctylphenyl-octaglycol ether and 2 parts by weight of a protective colloid, for example, sulphite waste liquor, are ground together to form a fine powder in a stud mill. This powder is suitable for suspension in water.

EXAMPLE III

A pulverulent material capable of easy suspension in water is obtained by mixing and grinding 25 parts by weight of the compound of the formula I and 3 parts by weight of tertiary dodecylmercaptoundecaglycol ether, 7 parts by weight of pulverulent silica gel and 65 parts by weight of kaolin.

EXAMPLE IV

20 Parts by weight of the compound of formula I together with 9 parts by weight of isooctylphenyl-heptaglycol ether, 41 parts by weight of mesityl oxide and 30 parts by weight of cyclohexanone are stirred together to form a clear solution which may be used as a liquid spraying agent concentrate.

EXAMPLE V 50 g of the compound of formula I, 15 g of pulverulent soy bean albumin extract (spray soy), 5 g of commercially available dextrin, 18 g of a sulphonated condensation product of naphthalene and formaldehyde, 4 g of the sodium salt of alkylbenzenesulphonate, 2 g of ammonium caseinate and 6 g of colloidal silicic acid (Santocel) are ground together in a ball mill to form a wettable powder.

EXAMPLE VI 80 g of the compound of formula I, 5 g of sulphite cellulose powder (calcium salt), 5 g of a pulverulent mixture consisting of ¾ of soy bean albumin extract (spray soy) and ¼ of dextrin, and 10 g of Santocel are finely ground in a ball mill together with 200 ml of water.

A finely dispersed suspension is obtained which, if desired after further thickening by means of polyvinyl alcohol or carboxymethyl cellulose, may be used as a pastyform suspension concentrate. Its consistency may be varied within wide limits depending on the amount of thickening agent added.

EXAMPLE VII

The suspension obtained according to Example VI, without addition of thickener, is carefully evaporated to dryness in a vacuum and subsequently ground in a ball mill; in this way a wettable powder is obtained which shows excellent suspension properties when it is stirred into water to give a preparation ready for use.

EXAMPLE VIII

A solution in acetone of 20 g of the compound of formula I is sprayed on 180 g of pumice granulate having a grain size of 0.3 to 1 mm and the solvent is then removed in the vacuum of a water pump at 40°–60° C. A well flowing grainy granulate is obtained.

EXAMPLE IX

5 Parts by weight of the compound of formula I and 85 parts by weight of bentonite are put into a mixer and 10 parts by weight of diethyleneglycol are sprayed in while mixing continuously. The resulting mixture is kneaded in a kneader and then granulated to a grain size of 0.5 to 1 mm.

The following Examples 1 and 2 describe and set out particulars of greenhouse tests carried out with the compound I and also Diuron for comparison purposes.

EXAMPLE 1

Pre-emergent treatment

Seed dishes measuring 30 × 40 cm are filled to a depth of 6 cm with a mixture of peat culture substrate No.1 (Obtainable from Torfstreuverband GmbH., 29 Oldenberg, Germany) and sand. The exposed surface of the peat culture and sand mixture is sprayed with 50 ml of a certain percentage by weight solution of herbicide, and six species of seed are then sown in each dish. The number of seeds sown for each plant species depends on the seed germination potential and also the initial growth size of the particular seed plant. After sowing of the seeds, the treated surface is covered with a thin layer about 0.5 cm deep of the peat culture and sand mixture.

The prepared seed dishes are kept for 28 days at a temperature of 20° to 24° C and 14 to 17 hours normal summer daylight each day.

Determination of the herbicidal effect of the particular herbicide is made after the 28 days period. The determination involves a visual evaluation of the degree and quality of damage to the various seed plants. A rating number between 1 and 9, dependent on the extent of damage to the seed plant is allocated to each plant species.

As will be appreciated by those in the art, this Examle gives an indication of the degree of biological as opposed to mechanical, selectivity since the seeds are sown into a herbicidally treated layer of peat culture and sand mixture and then covered with a further layer of the same.

The results obtained with compound I and Diuron are set out in the following Tables 1 and 2. The weeds employed in the tests are
*Plantago Major*
*Amaranthus retroflexus*
*Capsella bursa-pastoris*
*Echinochloa crus-galli*
*Senecio vulgaris*
*Galium aparine*
*Stellaria media*
*Chenopodium album*
*Alopecurus pratensis*
*Alopecurus myosuroides*
*Lolium perenne*
*Setaria sp.*

TABLE 1

COMPOUND 1

RATING NUMBERS ALLOCATED IN PRE-EMERGENCE TESTS

| Dose % w/v | 0.008 | 0.02 | 0.04 | 0.06 | 0.2 |
|---|---|---|---|---|---|
| CARROT | 0 | 0 | 2 | 0 | 4 |
|  | 0 | 0 | 0 | 0 | 2 |
|  | 0 | 0 | 0 |   | 3 |
|  | 0 |   | 0 |   | 5 |
|  | 0 |   | 0 |   |   |
|  |   |   | 0 |   |   |
| MEAN RATING NUMBER | 0 | 0 | 0.3 | 0 | 3.5 |
| WHEAT | 0 | 0 | 1 | 2 | 4 |
|  | 0 | 0 | 0 | 2 | 4 |
|  | 0 | 0 | 0 |   | 3 |
|  | 0 |   | 0 |   | 4 |
|  | 0 |   | 1 |   |   |
|  |   |   | 0 |   |   |
|  |   |   | 0 |   |   |
| MEAN RATING NUMBER | 0 | 0 | 0.3 | 2 | 3.8 |
| WEEDS (mean of 12 weed species) | 3.8 | 8.2 | 7.7 | 8.6 | 7.8 |
|  | 3.8 | 8.5 | 8.4 | 8.8 | 8.2 |
|  | 6.8 | 7.2 | 6.4 |   | 7.0 |
|  | 5.7 |   | 8.4 |   | 8.6 |
|  | 4.2 |   | 8.1 |   |   |
|  |   |   | 8.5 |   |   |
|  |   |   | 6.7 |   |   |
| MEAN RATING NUMBER | 4.8 | 7.6 | 7.7 | 8.7 | 7.9 |

TABLE 2

COMPOUND - Diuron

RATING NUMBERS ALLOCATED IN PRE-EMERGENCE TESTS

| Dose % w/v | 0.04 | 0.06 | 0.2 |
|---|---|---|---|
| CARROT | 2 | 8 | 9 |
|  | 2 | 9 | 8 |
|  | 1 |   |   |
|  | 8 |   |   |
| MEAN RATING NUMBER | 3.2 | 8.5 | 8.5 |
| WHEAT | 7 | 9 | 8 |
|  | 7 |   | 9 |
|  | 7 |   |   |
|  | 9 |   |   |
| MEAN RATING NUMBER | 7.5 | 9 | 8.5 |
| WEEDS (mean of 12 weed species) | 5.8 | 8.6 | 7.3 |
|  | 5.5 | 8.7 | 7.8 |
|  | 6.0 |   |   |
|  | 8.1 |   |   |
| MEAN RATING NUMBER | 6.4 | 8.7 | 7.6 |

As will be observed from the Tables, at the 0.06 and 0.2 concentrations, the degree of damage caused by diuron in wheat and carrots is the same as or higher than that in the weeds. At the 0.04 concentration, in wheat, again the degree of damage is greater than that caused in the weeds and in carrots is 50% that caused in weeds. In no case tested could diuron be said to exercise biological selectivity in carrots or wheat.

In the case of treatment with the compound of formula I on the other hand, at the 0.04 concentration 200% more damage is caused in the weeds than in either the wheat or the carrots. At the 0.06 concentration, complete selectivity is to be observed with regard carrots with appreciable damage to the weeds, and more than four times more damage in the wheat than the weeds is observed. Even at the highest concentration of 0.2, it can be seen that the degree of damage to the wheat and carrots is 50% less than that in the weeds. At the lower concentrations of 0.008 and 0.02, complete selectivity with appreciable damage to the weeds is observed.

The conclusion to be drawn is that the compound of formula I at all concentrations tested, maintains a damage differential between, on the one hand the carrots and the wheat, and on the other hand the weeds, and so a definite biological selectivity for the weeds. Diuron on the hand shows no such damage differential and indeed, generally, more damage is observed in the wheat and carrots than in the weeds.

EXAMPLE 2

Post-emergent treatment

A procedure similar to that of the pre-emergence test described above is followed, excepting that the 50 ml of herbicide solution is applied when the seed plants are at a 2–4 leaf stage. In order that uniform treatment of various seed plants may be effected at a time when each of the plant species has reached the 2–4 leaf stage, the various seed species are sown in time staggered relationship.

As with the pre-emergence test, the prepared seed dishes treated with herbicide are kept for 28 days under the greenhouse conditions described. The determination of the herbicidal effect of the particular herbicide again involves a visual evaluation of the degree and quality of damage to the various seed plants, and an allocation of a rating number in the manner described.

The results obtained with compound I and Diuron are set out in the following Tables 3 and 4. The weeds in the tests are the same as listed in the above pre-emergent test.

TABLE 3

COMPOUND 1

RATING NUMBERS ALLOCATED IN POST-EMERGENCE TESTS

| Dose % w/v | 0.008 | 0.02 | 0.04 | 0.06 | 0.2 |
|---|---|---|---|---|---|
| CARROT | 0 | 0 | 0 | 0 | 1 |
|  | 0 | 3 | 0 |   | 0 |
|  | 0 |   | 0 |   | 5 |
|  | 0 |   | 0 |   | 2 |
|  | 0 |   | 0 |   | 2 |
|  | 0 |   | 0 |   |   |
|  |   |   | 0 |   |   |
|  |   |   | 1 |   |   |
| MEAN RATING NUMBER | 0 | 1.5 | 0.1 | 0 | 2.0 |
| WHEAT | 1 | 3 | 0 | 0 | 0 |
|  | 0 | 0 | 0 |   | 5 |
|  | 0 | 3 | 0 |   | 3 |
|  | 0 |   | 1 |   | 2 |
|  | 0 |   | 3 |   | 5 |
|  | 2 |   | 0 |   |   |
|  |   |   | 2 |   |   |
|  |   |   | 0 |   |   |
| MEAN RATING NUMBER | 0.5 | 1.5 | 0.8 | 0 | 3.0 |
| WEEDS (mean of 12 weed species) | 4.4 | 8.0 | 8.5 | 8.8 | 8.9 |
|  | 5.3 | 8.3 | 7.6 |   | 8.9 |
|  | 7.1 |   | 8.7 |   | 8.9 |
|  | 5.4 |   | 8.2 |   | 8.9 |
|  | 4.4 |   | 8.9 |   | 8.9 |
|  | 4.7 |   | 7.0 |   |   |
|  |   |   | 7.5 |   |   |
|  |   |   | 8.1 |   |   |
| MEAN RATING NUMBER | 5.2 | 8.2 | 8.1 | 8.8 | 8.9 |

TABLE 4

COMPOUND - Diuron

RATING NUMBERS ALLOCATED IN POST-EMERGENCE TESTS

| Dose % w/v | 0.04 | 0.2 |
|---|---|---|
| CARROT | 4 | 9 |
|  | 2 | 9 |
|  | 3 | 9 |
|  | 8 |   |
| MEAN RATING NUMBER | 4.2 | 9.0 |
| WHEAT | 2 | 5 |
|  | 6 | 8 |
|  | 2 | 7 |
|  | 0 |   |
| MEAN RATING NUMBER | 2.5 | 6.9 |
| WEEDS (mean of 12 weed species) | 6.6 | 8.1 |
|  | 7.8 | 8.8 |
|  | 7.3 | 9.0 |
|  | 6.9 |   |

TABLE 4-continued

COMPOUND - Diuron

RATING NUMBERS ALLOCATED IN POST-EMERGENCE TESTS

| MEAN RATING NUMBER | 7,2 | 8,6 |
| --- | --- | --- |

The following Examples 3 to 6 are illustrative of the method of the present invention. These Examples concern field tests in the open, and confirm the indications obtained in a series of greenhouse tests, including those described above.

EXAMPLE 3

Combating of weeds in cereals, small plot test in the open

Plots of a size of 5 square meters are separated off in a cereal field sown with wheat. When the germinated cereal has reached the 2 to 5 leaf stage, the soil plots are sprayed with aqueous suspensions of diuron and the compound of formula I respectively in a quantity corresponding to 1000 liters of liquor and 2.5 kg of active agent per hectare. After 3 weeks the weeds belonging to the group of mono- and dicotyledons, i.e. *Alopecurus spp.* (*A. myosuroides, A. pratensis*), *Amaranthus retroflexus, Agrostis spica-venti, Atriplex patula, Capsella bursa-pastoris, Chenopodium album, Echniochloa crus-galli, Galeopsis tetrahit, Lamium purpureum, Poa annua, Polygonum convolvulus, Polygonum persicaria, Papaver rhoeas, Portulaca oleracea, Raphanus raphanistrum, Stellaria media* and *Thlaspi arvense*, are destroyed. No damage can be ascertained in the case of the cereal treated with the compound of formula I, but the soil treated with Diuron shows total damage to the cereal plants. A similar effect was observed in winter and summer barley.

EXAMPLE 4

Selective combating of weeds in winter by post-emergence process, small plot test in the open air Plots of the size of 5 square meters, having mainly a weed growth of *Alopecurus myosuroides, Agrostis spica-venti* and *Avena fatus* in addition to dicotyledons, are sprayed at a period when the winter wheat has 3-5 leaves with an aqueous suspension of the compound of formula I in an amount corresponding to 3.5 kg per hectare. Evaluation after 28 days shows a complete herbicidal effect with insignificant damage to the winter wheat.

In plots of land of the same size, treatment for purposes of comparison with Diuron in the same amount results in total damage to the winter wheat.

The compound of formula I is used with similar success for combating weeds in summer wheat, winter and summer barley, and winter and summer rye. Winter wheat is likewise undamaged when the amount of compound I is increased to 6 kilogram per hectare.

EXAMPLE 5

Selective combating of weeds in carrots by pre-emergence process, small plot test in the open Carrot seeds are sown in freshly dug fallow plots of land of a size of 5 square meters, an earth covering is applied and on the same day spraying with an aqueous suspension of diuron and the compound of formula I respectively is effected, the amount corresponding to 4.5 kg of each active agent per hectare. A plot is kept untreated as a blank. Evaluation of the test after 3 weeks gives the results described in the following Table.

TABLE

| Active Agent | Herbicidal Effect | Damage to Carrots |
| --- | --- | --- |
| Diuron | some plants of Plantago major | complete |
| Compound of Formula I | completey free of weeds | insignificant |
| Blank | germinated weeds: Amaranthus retroflexus, Echinochloa crus-galli, Galinsoga parviflora, Plantago major, Poa annua, Sinapis arvensis, Stellaria media, Polygonum persicaria, Polygonum convolvulus, Raphanus raphanistru, Capsella bursa-pastoris and Galeopsis tetrahit. | |

This test shows the excellent biological selective herbicidal effect of the compound of formula I as compared with the active agent used for purposes of comparison; no damage to the culture resulted when 6 kg/hectare of the compound of formula I were applied.

EXAMPLE 6

Selective combating of weeds in carrots by post emergence, small plot test in the open Plots of the size of 5 square meters having mainly a weed growth of *Amaranthus retroflexus, Echinochloa crus-galli, Galinsoga parviflora, Plantago major* and *Sinapis arvensis* and on which carrots had germinated after seeds of carrots had been sown, are treated at a time when the carrots have reached the 4 leaf stage with aqueous suspensions of diuron and the compound of formula I respectively in an amount corresponding to 4.5 kg per hectare. One plot is kept untreated as a blank. Evaluation after 28 days gives the results shown below:

| Active Agent | Herbicidal Effect | Damage to Carrots |
| --- | --- | --- |
| Diuron | some plants of Plantago major | complete |
| Compound of formula I | completely free of weeds | insignificant |

| Active Agent | Herbicidal Effect | Damage to Carrots |
|---|---|---|
| Blank | strong weed growth | |

The excellent selectivity of the compound of formula I on post-emergence application is again confirmed together with superior herbicidal effect. A similarly good result is obtained when using the wettable powder described in Example VII.

EXAMPLE 7

Selective control of weeds in winter barley

Field plots were sown with winter barley seeds (*Pella* variety). Some plants were treated pre-emergence of the barley and others post-emergence at the three leaf to tillering stage at dosages of 4 and 12 kg/hectare of the compound of formula I*. One plot was not treated to serve as a control plot. In general, weed infestation in all cases were mainly *Alopecurus myosuroides* with some broad leaf infestation. At the harvesting stage, the weed infestation was assessed in both the pre- and post-emergence plots and compared with the control. In every case, excellent weed control was observed. The crops were then harvested and the yield per acre in relation to the control plot was determined. The results are set out below (the control yield being taken as 100%).

| | Pre | Post |
|---|---|---|
| 4 kg/hectare | 110% | 118% |
| 12 kg/hectare | 115% | 118% |

EXAMPLE 8

Selective weed control in barley

Field plots (40 m²) were sown with winter barley (Ager and Astrix varieties) and treated with the compound of formula I* at the 3 leaf stage at a dosage of 3 kg/hectare. Weed infestation was mainly *Alopecurus myosuroides*. The degree of weed control at harvesting time was determined by visual comparison with a control untreated plot. The degree of weed control was assessed at approximately 80% with no appreciable damage to the barley.

*[The compound of formula I is applied in the form of the formulation described in Example II above in aqueous suspension.]

What is claimed is:

1. A method of selectively combating weeds in a barley locus to be protected from weeds which comprises applying to the locus the compound N-(3-chloro-4-methoxyphenyl)-N',N'-dimethylurea in an amount of from 2 to 10 kilograms per hectare of locus.

2. The method of claim 1, wherein the amount of said compound applied to the locus is from 2 to 6 kilograms per hectare of locus.

3. The method of claim 2, wherein the barley locus contains weed grasses.

4. The method of claim 1, wherein the compound is applied pre-emergent with respect to the barley.

5. The method of claim 1, wherein the compound is applied post-emergent with respect to the barley.

* * * * *